(12) United States Patent
Clausen et al.

(10) Patent No.: US 7,858,125 B2
(45) Date of Patent: Dec. 28, 2010

(54) MULTI-COMPONENT BIOCIDE COMPOSITION FOR WOOD PROTECTION

(75) Inventors: Carol A. Clausen, DeForest, WI (US); Vina W. Yang, Verona, WI (US); Michael H. West, Senatobia, MS (US); Erlene West, legal representative, Senatobia, MS (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 871 days.

(21) Appl. No.: 11/726,359

(22) Filed: Mar. 21, 2007

(65) Prior Publication Data

US 2007/0224289 A1 Sep. 27, 2007

Related U.S. Application Data

(60) Provisional application No. 60/784,563, filed on Mar. 22, 2006.

(51) Int. Cl.
*A01N 59/14* (2006.01)
*A01N 43/78* (2006.01)
*A01N 33/02* (2006.01)
*A01N 37/02* (2006.01)
*A01N 31/02* (2006.01)

(52) U.S. Cl. .............. 424/659; 514/365; 514/557; 514/642; 514/663; 514/671; 514/738

(58) Field of Classification Search ............. 424/659; 514/394, 557, 642, 365, 663, 671, 738
See application file for complete search history.

(56) References Cited

U.S. PATENT DOCUMENTS

| | | | |
|---|---|---|---|
| 4,388,215 A | 6/1983 | Ishida et al. | |
| 5,100,583 A | 3/1992 | Malouf et al. | |
| 5,221,758 A | 6/1993 | Maynard | |
| 5,540,954 A | 7/1996 | Nicholas et al. | |
| 5,601,849 A | 2/1997 | Dunstan et al. | |
| 5,892,048 A | 4/1999 | Kishimoto et al. | |
| 6,262,097 B1 | 7/2001 | Kovacevic | |
| 6,441,016 B2 * | 8/2002 | Goettsche et al. | ........... 514/383 |
| 6,844,081 B2 | 1/2005 | Hart et al. | |

OTHER PUBLICATIONS

Clausen et al "Protecting wood from mould decay & termites w. multi-component biocide sys." Int'l Biodeter & Biodeg. 2007, p. 20-24, 59, Elsevier, Amsterdam, NL.

Clausen et al "Multicompon. biocide sys. protect wood from decay fungi, etc." Paper prep for 35th ann. meeting, Jun. 10, 2004, Int'l research grp. on wood preserv. Ljubljana, SI.

Clausen et al "Long-term efficacy of wood dip-treated with multi-compon. biocides," Paper prep. for 36th ann. meet., Apr. 2005, Int'l res. grp. on wood protect'n; Bangalore, IN.

* cited by examiner

*Primary Examiner*—John Pak
(74) *Attorney, Agent, or Firm*—John D. Fado; Lesley D. Shaw; Janet I. Stockhausen

(57) ABSTRACT

The present disclosure generally relates to a multi-component biocide composition comprising a borate component in combination with an azole component to both inhibit mold fungi, decay fungi, such as brown-rot fungi and white-rot fungi, and to resist insect infestation.

1 Claim, 2 Drawing Sheets

MULTI-COMPONENT BIOCIDE COMPOSITION FOR WOOD PROTECTION

BACKGROUND OF DISCLOSURE

The present disclosure generally relates to a multi-component biocide composition that provides improved protection against mold growth, decay, and termite infestation of wood-based materials. Specifically, the multi-component biocide composition comprises a borate component in combination with an azole component to both inhibit decay fungi such as brown-rot fungi and white-rot fungi, mold fungi, and to resist insect infestation.

While lumber and other wood-based materials derived from trees are not perishable, they are, nevertheless, susceptible to a host of natural destructive forces. These primarily include attack by insects, such as termites, carpenter ants and the like and fungi such as brown-rot (*Poria* Sp.) and white-rot (*Polyporous* Sp.) wood decay fungi (*Poria placenta*), as well as mold fungi. Decay fungi are primarily responsible for deterioration of wood (i.e., loss of structural integrity), while mold fungi grow on the surface of wood and do not affect the wood structure. Rather, mold fungi produce copious amounts of spores and can cause health concerns in both humans and animals. Specifically, decay fungi colonize wood over a period of time when the wood moisture content is above fiber saturation (e.g., approximately 30% (by weight) moisture) and the temperature is between approximately 10° C. and approximately 35° C. Mold growth can occur on the wood surface in 24 to 48 hours under conditions of high humidity (e.g., greater than approximately 30° C.) or when in the presence of free water, such as from a leak or flood. Such fungal growth in residential structures in the U.S. accounts for billions of dollars in damages annually.

The increase in mold growth on indoor wood-based materials in residential structures has further lead to an increase in public concern about indoor air quality and health concerns. To date, moisture management through proper construction practices and site drainage provides the best defense against mold growth.

Furthermore, as noted above, wood-based materials are susceptible to insects in addition to fungal attacks. Various species of insects pose problems for living trees and structural wood. For example, *Coptotermes formosanus* is a major worldwide pest that, unlike other subterranean termites, can establish colonies that do not touch the ground. These termites and other subterranean termites have cost the U.S. over $2 billon annually in damages to residential structures. As such, numerous measures have been made to protect against such infestations. Specifically, three principal methods have been used in the past to control insect growth on wood-based materials both indoors and outdoors: (1) chemical and physical barriers to prevent attacks; (2) wood preservatives and termiticides used to protect infested and susceptible wood, and (3) destruction of termite colonies by excavation of the nest.

Current treatments, however, have not been found completely satisfactory as many compounds in the treatments are environmentally hazardous, many pose safety risks to humans and animals, and create difficult and expensive disposal problems. This is particularly a problem when the treatment is for indoor use such as in the treatment of wood-based materials designed for residential structures. Furthermore, treatments that are safe for indoor use, for example, borate (termiticide), have not been found effective in controlling mold. Specifically, many mold fungi are inherently resistant to UV rays, the numerous chemicals that have been developed, and even most wood preservatives that have been used as protective treatments.

As such, there continues to be a need for a biocide composition for treating wood-based materials that is effective against mold and decay fungal growth and can also prevent insect infestation. Additionally, it would be advantageous if the biocide composition is suitable for indoor use, that is, the biocide composition is non-toxic, nonvolatile, substantially odorless, and hypoallergenic.

SUMMARY OF THE DISCLOSURE

The present disclosure relates to a multi-component biocide composition that is non-toxic, nonvolatile, substantially odorless, and hypoallergenic. The biocide composition provides improved protection against mold growth, decay fungi growth, and termite infestation of indoor wood-based materials. In one embodiment, the multi-component biocide composition comprises a borate component in combination with an azole component and other components to both inhibit the growth of mold fungi, decay fungi such as brown-rot fungi and white-rot fungi, and to resist insect infestation.

As such, the present disclosure is directed to a biocide composition comprising a borate component, an azole component, a glycol component, a quaternary amine component, and propionic acid.

The present disclosure is further directed to a biocide composition comprising boric acid, thiabendazole, dimethylcocoamine, propionic acid, and propylene glycol.

In addition to the biocide composition, the present disclosure is additionally directed to using the biocide composition to treat wood-based materials to prohibit mold growth, decay, and termite infestation.

Specifically, in one embodiment, the present disclosure is directed to a method for treating wood-based materials to prevent mold growth, decay, and termite infestation. The method comprises applying a biocide composition to the wood-based material. The biocide composition comprises a borate component, an azole component, propylene glycol, dimethylcocoamine, and propionic acid.

Other objects and features will be in part apparent and in part pointed out hereinafter.

DETAILED DESCRIPTION OF THE DISCLOSURE

Figure 1:
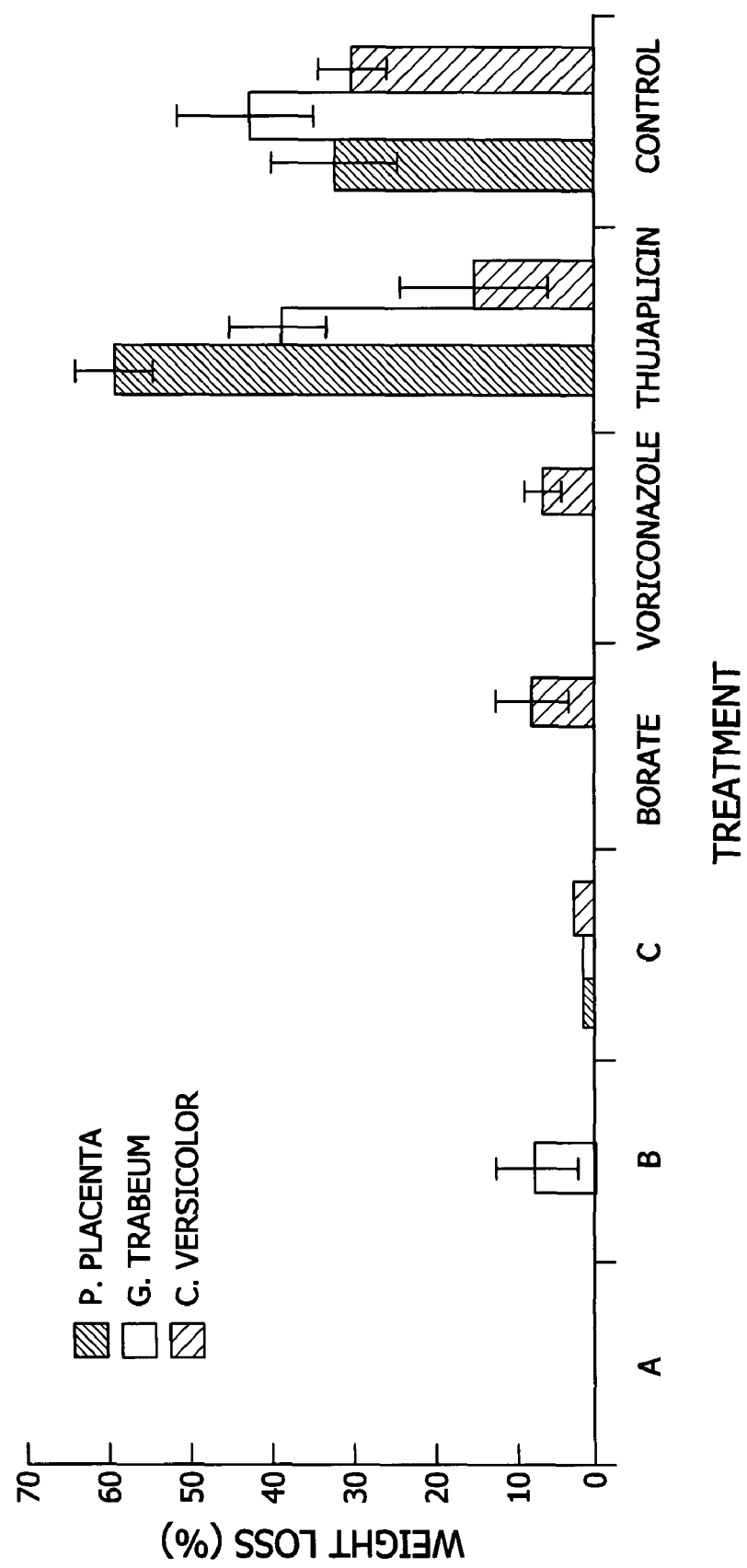
FIG. 1 is a graph depicting the results of the decay analysis on the wood-based materials treated with the various biocide compositions of Example 4.

The present disclosure generally relates to a multi-component biocide composition that provides improved protection against mold growth, decay, and termite infestation of wood-based materials. One aspect of the present disclosure is directed to a multi-component biocide composition comprising a borate component and an azole component in combination with various other components to both inhibit growth of mold fungi, decay fungi such as brown-rot fungi and white-rot fungi, and to resist insect infestation.

As noted above, millions of dollars are consumed annually in the U.S. in attempts to protect wood-based materials such as lumber used in residential homes from damage caused by mold growth, decay, and insect infestation. Mold infestation of indoor wood-based materials has further produced a growing public concern about indoor air quality issues. In response, numerous biocide and insecticide products have been produced. Current products, however, have not been found to effectively inhibit mold growth, decay fungi, and prevent infestation by insects such as termites. Furthermore, many current biocide products have been found to be environmentally hazardous and are not suitable for indoor use.

The biocide composition of the present disclosure provides an improved efficacy for inhibiting growth of mold and decay fungi and preventing termite infestation. Specifically, the biocide composition is capable of preventing spore germination and can provide for long-term protection against both fungal growth and insect infestation under conditions of high humidity. Furthermore, the biocide composition is non-toxic, non-volatile, substantially odorless, and hypoallergenic and, as such, is desirable for indoor use.

In one embodiment, the biocide composition of the present disclosure comprises a borate component, a quaternary amine component, propionic acid, a glycol component, and an azole component. Optionally, the biocide composition can also include thujaplicin.

Borate Component

Specifically, the borate component of the biocide composition comprises at least one borate compound as a base. At low concentrations, borates have been found to inhibit decay fungi such as *Postia placenta*, *Gloeophyllum trabeum*, and *Coriolus versicolor*. Furthermore, borates are known inhibitors of insect infestation such as the infestation of wood-based materials by termites.

Suitable borate components for use in the biocide compositions include, for example, boric acid, zinc borate, disodium octaborate tetrahydrate, and combinations thereof. One particularly preferred borate compound for use as the borate component is boric acid.

Typically, the borate component is present in the biocide composition in an amount of from about 1 milligram (mg) of borate component per milliliter (ml) of biocide composition to about 5 mg of borate component/ml of biocide composition. More suitably, the borate composition is present in the biocide composition in an amount of about 1 mg/ml.

While borates are known to inhibit decay fungi, borates have not been found to be effective against mold fungal growth. Common mold fungi that infest wood-based materials include *Aspergillus niger*, *Penicillium chrysogenum*, and *Trichoderma viride*. As such, in addition to the borate component, the biocide composition of the present disclosure comprises additional components to prevent mold fungal growth. Surprisingly, when the additional components are combined with the borate component, not only can the biocide composition prevent mold fungal growth, but the efficacies of the composition in inhibiting the growth of both mold and decay fungi and termite infestation are increased as compared to using any of the components of the biocide composition alone.

Quaternary Amine Component

In addition to the borate component, the biocide composition further comprises a quaternary amine component. Quaternary amines are known to inhibit decay fungal growth.

Suitable quaternary amine components include dimethylcocoamine, didecyldimethyl ammonium chloride (DDAC), and alkyldimethylbenzylammonium chloride (BAC), and combinations thereof. One particularly preferred quaternary amine component for use in the biocide composition of the present disclosure is dimethylcocoamine.

Typically, the biocide composition comprises the quaternary amine component in an amount of from about 0.010 milliliters of quaternary amine per milliliter of biocide composition to about 0.024 of quaternary amine per milliliter of biocide composition. More suitably, the quaternary amine component is present in the biocide composition in an amount of from about 0.011 ml/ml to about 0.024 ml/ml and, even more suitably, in an amount of about 0.011 ml/ml.

It is desirable that the quaternary amine component be soluble in the biocide composition to create homogeneity of the solution and allow for an easier application of the biocide composition to the wood-based material. While the borate component (e.g., boric acid) is capable of solubilizing the quaternary amine component, typically the borate component is not acidic enough to form the salt of the fatty amine when combined with the quaternary amine component alone. Specifically, without additional components to solubilize the quaternary amine component, the quaternary amine component would separate from the remaining components in the composition and float to the top of the mixture. As such, additional components are needed to solubilize the quaternary amine component. Specifically, in one particularly preferred embodiment, propionic acid is included in the biocide composition to aid in the solubilizing of the quaternary amine component. Additionally, propionic acid has been found to show some degree of inhibition against the growth of decay fungi.

Typically, in order for the biocide composition to be stable, the solubilizer, such as propionic acid, is present in the biocide composition in a weight ratio of solubilizer to quaternary amine component of from about 1:1 to about 1:3 and, more suitably about 1:2.2. More suitably, the solubilizer is present in the biocide composition in a volume ratio of solubilizer to quaternary amine component of from about 0.01 ml/ml:0.01 ml/ml to about 0.004 ml/ml:0.012 ml/ml. Even more suitably, the solubilizer is present in the biocide composition in a volume ratio of solubilizer to quaternary amine component of about 0.005 ml/ml:0.011 ml/ml.

Glycol Component

Additionally, the biocide composition of the present disclosure includes a glycol component. The glycol component is included in the biocide composition of the present disclosure to stabilize the composition.

One suitable glycol component for use as a stabilizer for the biocide composition is propylene glycol. The glycol component is typically included in the biocide composition of the present disclosure in an amount of from about 0.002 ml/ml to about 0.008 ml/ml. More suitably, the glycol component is present in the biocide composition in an amount of from about 0.003 ml/ml to about 0.006 ml/ml and, even more suitably, about 0.003 ml/ml.

Azole Component

As noted above, the borate component does not satisfactorily inhibit mold fungal growth when used alone. As such, the biocide composition of the present disclosure further comprises an azole component. Azole compounds are known to inhibit both mold and decay fungal growth as they target ergosterol synthesis, which is the predominant component of fungal cell membranes. Some first generation triazoles have a complicated mode of action involving inhibition of several membrane-bound enzymes as well as lipid biosynthesis. Second generation triazoles, such as voriconazole, act in part by inhibiting cytochrome P-450-dependent 14α-sterol demethylase. These compounds, however, are not effective in preventing insect infestation such as termite infestation.

Suitable azole components for use in the biocide composition of the present disclosure include triazole compounds. For example, voriconazole, thiabendazole, propiconazole, tebuconazole, sodium triazole, difluconazole, clotrimazole, itraconazole, miconazole, and combinations thereof are suitable for use as the azole component. Particularly preferred azole components include voriconazole and thiabendazole.

Typically, the biocide composition comprises an azole component in an amount of from about 0.05 mg/ml biocide composition to about 2.0 mg/ml biocide composition. More suitably, the azole component is present in the biocide composition in an amount of about 1.0 mg/ml.

Optional Component

As noted above, the biocide composition of the present disclosure can further include optional components. For example, in one particularly preferred embodiment, the biocide composition further comprises thujalicin. Thujalicin is an extract available from Western Red Cedar. The addition of thujalicin to the biocide composition of the present disclosure has been found to impart some degree of water resistance. Furthermore, thujalicin has been found to create a minor odor of cedar oil to the biocide composition, which may be suitable for specific applications, such as when using the biocide composition as an exterior finish or sealer for wood siding or decking.

When added to the biocide composition, the thujalicin is typically present in the biocide composition in an amount of from about 0.25% (by weight total biocide composition) to about 1.5% (by weight total biocide composition). More suitably, thujalicin is present in the biocide composition in an amount of about 0.5% (by weight total biocide composition).

Treating Wood-Based Materials with Biocide Composition

In addition to the biocide composition, the present disclosure is additionally directed to methods of using the biocide composition on wood-based materials, particularly indoor wood-based materials, for inhibiting both mold and decay fungal growth and insect infestation. Specifically, in one particularly preferred embodiment, wood-based materials are treated to prevent mold and decay fungal growth and insect infestation by applying the biocide composition of the present disclosure directly to the wood-based material.

To obtain the biocide composition, the borate component, propionic acid, quaternary amine component and glycol component of the composition, as described more fully above, are combined to form an aqueous stock solution with mechanical stirring. Specifically, once the components are combined, the stock solution is diluted with water to create a solution containing from about 2% (by weight) to about 4% (by weight) biocide composition. The azole component is prepared separately. Specifically, if a water soluble azole (e.g., voriconazole) is to be used in the biocide composition, the water soluble azole is added directly to the aqueous stock solution containing the biocide composition with mechanical stirring. Alternatively, if an azole having low solubility is to be used (e.g., thiabendazole), the azole must first be dissolved in a 70% (by volume) ethanol solution prior to being stirred into the aqueous stock solution containing the biocide composition.

Once the aqueous stock solution containing the biocide composition is obtained, the biocide composition is applied to the wood-based materials. As noted above, the biocide compositions are desirable for indoor use. As such, indoor wood-based materials such as lumber for residential housing are particularly preferred. Specifically, suitable wood-based materials for use with the biocide compositions of the present disclosure include, for example, plywood, oriented strandboard, flakeboard, and paper-coated products such as gypsum. The wood-based materials may be produced from any suitable wood used for lumber or in wood-based products. More specifically, the wood-based materials are typically materials produced from Douglas-fir, Aspen, Southern Yellow Pine, and the like.

The biocide composition can suitably be applied to the wood-based materials using any means known in the art. Specifically, in one particularly preferred embodiment, the wood-based material is dip-coated with the biocide composition. Specifically, when the biocide composition is applied to the wood-based material using a dip-coating method, the wood-based material is typically dipped into a bath of biocide composition for a period of from about 10 seconds to about 60 seconds and, more suitably, about 15 seconds to ensure complete coating of the biocide composition onto the wood-base material.

In another embodiment, the biocide composition is applied to the wood-based material by spray-coating. To spray-coat the wood-based material, the biocide composition is introduced into a spray bottle having a nozzle and the biocide composition is sprayed directly onto the wood-based material. Any size and shape of nozzle known in the art is suitable for use in applying the biocide composition to the wood-based material.

In yet another embodiment, the biocide composition is brush-coated onto the wood-based material. Any known method of brush-coating is suitable for use in this embodiment.

In still yet another embodiment, the biocide composition is pressure-treated into the wood-based material. To pressure-treat the biocide composition into the material, an initial vacuum of approximately $-75$ kPa (25 inches Hg) is maintained for 30 minutes. After 30 minutes, aqueous stock solution containing the biocide composition is added to a pressure treatment cylinder. The wood-based material to be treated with the biocide composition is then introduced into the pressure treatment cylinder containing the stock solution. The pressure treatment cylinder is maintained at a pressure of 1.03 MPa (150 lb/in$^2$) for approximately 2 hours. Following pressure treatment, the wood-based material is removed from the stock solution and air-dried.

Typically, when the biocide composition is applied to the wood-based material by dip coating, brush coating, or spray coating, the biocide composition is applied to the surface of the wood-based material in an amount of from about 10% (by weight wood-based material) to about 20% (by weight wood-based material). When the wood-based materials are pressure-treated with the biocide composition, the wood-based materials are treated with from about 15% (by weight wood-based material) to about 40% (by weight wood-based material) biocide composition and, more suitably, from about 20% (by weight wood-based material) to about 30% (by weight wood-based material).

In one embodiment, once the biocide composition is applied to the wood-based material, the wood-based material is post-treated. Specifically, once the biocide composition is applied to the wood-based material, the wood-based material can be stacked so as to facilitate air movement on all surfaces of the treated wood-based material and then allowed to air-dry at a temperature of from about 18° C. to about 30° C. In particularly preferred embodiments, the wood-based material can be dried using a fan to produce an active air flow over the treated surfaces of the wood-based material.

Furthermore, for applications in which it is known that the treated wood-based materials will be exposed to moisture, a sealer may additionally be applied according to the manufacturers' directions to increase service-life of the biocide composition.

Having described the invention in detail, it will be apparent that modifications and variations are possible without departing from the scope of the invention defined in the appended claims.

EXAMPLES

The following non-limiting examples are provided to further illustrate the present disclosure.

Example 1

In this Example, various compositions of biocide composition were prepared and tested for their efficacy in preventing mold fungal growth and decay fungal growth.

To prepare the biocide compositions, various amounts of components were added together. Various components (and their commercial suppliers) used in the biocide compositions are listed below:

Disodium octaborate tetrahydrate (DOT), a borate component available from U.S. Borax, Inc., Valencia, Calif.

Boric acid (0.1%), propionic acid (0.5%), and dimethylcocoamine (1.1%) (Bor-A+), an aqueous mixture of a borate component, propionic acid, and a quaternary amine component, available from Copper Care Wood Preservatives, Inc., Columbus, Nebr.

Voriconazole, an azole component, available from Pfizer, Inc., New York, N.Y.

Thiabendazole, an azole component, available from Sigma-Aldrich Chemical, St. Louis, Mo.

Thujaplicin (isopropyltropolone), available from Cedarome Canada, Inc., Montreal, Quebec.

The various components and amounts of the components used in the biocide compositions are shown in Table 1.

TABLE 1

| Sample | TREATMENT (mg/ml) | | |
|---|---|---|---|
| | Borate Component (mg/ml) | Azole Component (mg/ml) | Additional Component (% by total weight biocide composition) |
| 1 | DOT (20 mg/ml) | Thiabendazole (1 mg/ml) | Thujaplicin (0.5%) |
| 2 | DOT (20 mg/ml) | Thiabendazole (1 mg/ml) | Thujaplicin (1%) |
| 3 | DOT (20 mg/ml) | Thiabendazole (1 mg/ml) | 0 |
| 4 | DOT (20 mg/ml) | 0 | Thujaplicin (0.5%) |
| 5 | DOT (20 mg/ml) | 0 | Thujaplicin (1%) |
| 6 | Bor-A+ (20 mg/ml) | Thiabendazole (1 mg/ml) | Thujaplicin (0.5%) |
| 7 | Bor-A+ (20 mg/ml) | Thiabendazole (1 mg/ml) | Thujaplicin (1%) |
| 8 | Bor-A+ (20 mg/ml) | Thiabendazole (1 mg/ml) | 0 |
| 9 | Bor-A+ (20 mg/ml) | 0 | Thujaplicin (0.5%) |
| 10 | Bor-A+ (20 mg/ml) | 0 | Thujaplicin (1%) |
| 11 | 0 | 0 | Thujaplicin (1%) |
| 12 | 0 | 0 | Thujaplicin (0.5%) |
| 13 (Control A) | 0 | 0 | 0 |
| 14 (Control B) | 0 | 0 | 0 |

*20 mg/ml of Bor-A+ is equivalent to 1 mg/ml boric acid

The biocide compositions were first tested for the efficacy in preventing mold fungal growth. The mold fungi used in the mold growth analysis included *Aspergillus niger* 2.242 (available from University of Virginia, Charlottesville, Va.), *Penicillium chrysogenum* PH02 (an isolate provided by Forest Products Laboratory, Madison, Wis.) and *Trichoderma viride* ATCC 20476 (available from American Type Culture Collection, Rockville, Md.). The mold fungi were first prepared by growing the various mold fungi species on 2% malt agar. A mixed spore preparation was then prepared by washing the surface of a 2-week old culture of each fungus with 10 milliliters of sterile deionized (DI) water according to the American Society for Testing and Materials (ASTM) standard D4445-91 (1998). Spore suspensions were transferred to a spray bottle and diluted to 100 milliliters with DI water. The spray bottle was adjusted to deliver 1 milliliter inoculum/spray.

Specimens (7×20 millimeters cross section by 7 centimeters long) were cut from unseasoned southern yellow pine mill ends from a Mississippi sawmill and stored at 0° C. Average moisture content of the specimens was 48% by weight (n=3). Southern yellow pine oriented strand board (OSB) specimens (11×20 millimeters cross section by 7 centimeters long) were cut from a full sheet of OSB and conditioned to 70% relative humidity. Five replicate specimen stakes were dip-treated for approximately 15 seconds in each biocide composition and held in a covered container overnight according to the ASTM standard test method D4445-91 (1998). Specimens were then arranged over four layers of blotting paper that was saturated with 30 milliliters DI water and a polyethylene mesh spacer in sterile disposable Petri dishes (150×25 millimeters) (commercially available from B-D Falcon, Los Angeles, Calif.). Untreated stakes were dipped in DI water and served as Control A for water-based test chemicals. Additional stakes were dipped in 70% (by weight) ethanol to serve as Control B for test chemicals of low solubility.

All stake samples were then sprayed with 1 milliliter of mold spore inoculum, sealed in polyethylene bags to prevent drying, and incubated at 27° C. and 70% relative humidity for four weeks. Following incubation, stakes were individually rated for mold growth on a scale of 0-5 with 5 representing 100% coverage of the stakes with mold growth; 4 representing 80% coverage of the stakes with mold growth; 3 representing 60% coverage of the stakes with mold growth; 2 representing 40% coverage of the stakes with mold growth; 1 representing 20% coverage of the stakes with mold growth; and 0 representing no mold growth. The results are shown in Table 2.

TABLE 2

| | Mold Resistance Average Rating | |
|---|---|---|
| Sample: | Southern Pine specimen | OSB specimen |
| 1 | 5 | 1 |
| 2 | 4 | 0.4 |
| 3 | 5 | 0.6 |
| 4 | 4.2 | 2.6 |
| 5 | 5 | 0.6 |
| 6 | 0 | 0 |
| 7 | 0 | 0 |
| 8 | 0 | 0 |
| 9 | 0 | 0 |
| 10 | 0 | 0 |
| 11 | 3.2 | 5 |
| 12 | 0.6 | 0.4 |
| 13 | 5 | 5 |
| 14 | 5 | 5 |

As shown in Table 2, biocide compositions containing 20 mg/ml Bor-A+ with 1 mg/ml thiabendazole or 0.5 mg/ml thujaplicin completely inhibited a mixed mold suspension on both pine and OSB. Biocide compositions without Bor-A+ showed minor inhibition of mold growth due to the presence of thujaplicin. Furthermore, the control samples did not inhibit mold growth at all.

In addition to the mold fungi analysis above, the biocide compositions were tested for their efficacy in preventing decay fungal growth. The decay fungi used in the decay fungal growth analysis included *Postia placenta* MAD 698 (Fries) Lars. & Lomb., *Gloeophyllum trabeum* MAD 617 (Pers:Fries) Murrill, and *Coriolus versicolor* MAD 697 (L.: Fr.) Pilat. The decay fungi, all obtained from the Center of Forest Mycology Research (Forest Products Laboratory, Madison, Wis.) were maintained on 2% malt agar.

To test the biocide compositions' abilities to inhibit decay fungal growth, soil block culture bottles were prepared according to American Wood Preservers' Association (AWPA) E-10-01 (2003). Southern yellow pine feeders were inoculated with two brown-rot fungus, *P. placenta* and *G. trabeum* and maple feeders were inoculated with one white-rot fungus, *C. versicolor*. Bottles were incubated at 27° C. and 70% relative humidity for three weeks until the fungus completely colonized each feeder. Pre-weighed 1×1×1 centimeter southern yellow pine blocks, conditioned at 27° C. and 70% relative humidity, were vacuum-treated for 40 minutes at 172 kPa with each biocide composition. Blocks were conditioned at 25° C. for seven days, propylene oxide-sterilized, placed on actively growing feeders, and incubated at 27° C. and 70% relative humidity for twelve weeks. Following incubation, surface mycelia were brushed from each block. The blocks were then oven-dried at 60° C. for twenty-four hours and reconditioned at 27° C. and 70% relative humidity to a constant weight. The blocks were weighed and the average percentage weight loss was calculated. The results of the decay fungi analysis are shown in Table 3.

TABLE 3

| | Soil Block Test Average % weight loss ± SE | | |
|---|---|---|---|
| Sample: | P. placenta | G. trabeum | C. versicolor |
| 1 | 0.0 | 0.0 | 0.0 |
| 2 | 0.0 | 0.0 | 0.0 |
| 3 | 0.0 | 0.0 | 0.0 |
| 4 | 0.0 | 0.0 | 0.0 |
| 5 | 0.0 | 0.0 | 0.0 |
| 6 | 1.0 | 1.0 | 0.0 |
| 7 | 0.0 | 0.0 | 0.0 |
| 8 | 0.0 | 7.0 | 0.0 |
| 9 | 1.0 | 1.0 | 2.0 |
| 10 | 1.0 | 10.0 | 1.0 |
| 11 | 59 ± 5.3 | 38.4 ± 6.6 | 14.8 ± 9.3 |
| 12 | 59.4 ± 7.9 | 54.4 ± 9.3 | 29.6 ± 4.4 |
| 13 | 31 ± 8 | 42.4 ± 8.8 | 16.8 ± 6.8 |
| 14 | N/A | N/A | N/A |

As shown in Table 3, all individual biocide components of the biocide compositions alone, except thujaplicin, completely inhibited decay by *P. placenta*, *G. trabeum*, and *C. versicolor*. While thujaplicin alone did not inhibit decay, the biocide compositions containing a mixture of Bor-A+ and thujaplicin did provide inhibition of the decay fungi.

Example 2

In this Example, various biocide compositions were prepared and tested for their efficacy in preventing mold fungal growth. The efficacies of the biocide compositions were compared to compositions of commercially-used preservatives, fungicides, extracts, and pharmaceuticals that have known abilities to prevent mold fungal growth.

The various known preservatives, fungicides, extracts, and pharmaceuticals (and their commercial suppliers) are provided below:

Wood Preservatives and Additives: (each was diluted from 2% (v/v) of the concentrate with water in a series of dilutions until no mold inhibition occurred on wood test specimens when tested using the ASTM standard used in the mold growth analysis of Example 1.)

Disodium octaborate tetrahydrate (DOT) (5% w/v), a borate component, available from Pole Maintenance Co., Columbus, Nebr.

CuBor (5% v/v), a borate component, available from Sigma Chemical, St. Louis, Mo.

Food Preservatives: (each was diluted to 5% with water and each is commercially available from Sigma Chemical, St. Louis, Mo.)

Sodium acetate
Sodium benzoate
Calcium propionate
Potassium sorbate
Sodium formate
Sodium nitrite Plant Extractives: (each was diluted from 100% (v/v) in 70% ethanol solution to the point of no mold inhibition)

Thujaplicin (isopropyltropolone), available from Cedarome Canada, Inc., Montreal, Quebec.

Pine resin

Soybean ester, available from The Heavens Group, LLC, Rolla, Mo.

Pharmaceuticals and Agricultural Fungicides: (each was diluted with water to the point of no mold inhibition)

Triazole (5% w/v), an azole component, available from Sigma Chemical, St. Louis, Mo.

Sodium triazole (5% w/v), an azole component, available from Sigma Chemical, St. Louis, Mo.

Difluconazole (2% w/v), an azole component, available from Sigma Chemical, St. Louis, Mo.

Thiabendazole (5% w/v), an azole component, available from Sigma Chemical, St. Louis, Mo.

Voriconazole (1% w/v), an azole component, available from Sigma Chemical, St. Louis, Mo.

Miconazole (2% w/v), an azole component, available from Pharmacia Upjohn, Kalamazoo, Mich.

Clotrimazole (1% v/v suspension in polyethylene glycol), an azole component, available from TARO Pharmaceuticals, Bramalea, Ontario.

Samples of biocide composition were prepared using the following components (the composition is known hereinafter as "Borate-quat"):

Boric acid (5%), a borate component, available from National Boraxx, Cleveland, Ohio;

Propionic acid (25%), available from JT Baker, Phillipsburg, N.J.;

Dimethylcocoamine (55%), a quaternary amine component, available from Lonza, Inc., Fair Lawn, N.J.); and Polyethylene glycol (15%), a stabilizer, available from Sigma Chemical, St. Louis, Mo.

In some samples, the borate-quat biocide composition was further combined with components from the known preservatives, extracts, and pharmaceuticals listed above to produce the biocide composition.

The samples of preservatives, fungicides, extracts, pharmaceuticals, and biocide compositions and the amounts of the components used in the samples are shown in Table 4.

TABLE 4

| Sample | Test Chemical | (% test chemical by weight unseasoned pine sample) |
|---|---|---|
| Wood Preservatives and Additives: | | |
| 1 | DOT | 2.0 |
| 2 | DOT | 5.0 |
| 3 | CuBor | 2.0 |
| 4 | CuBor | 5.0 |
| 5 | Borate-quat | 0.5 |
| 6 | Borate-quat | 1.0 |
| 7 | Borate-quat | 1.5 |
| 8 | Borate-quat | 2.0 |
| 9 | Borate-quat | 2.5 |
| 10 | Borate-quat | 5.0 |
| Food Preservatives: | | |
| 11 | Sodium acetate | 5.0 |
| 12 | Sodium benzoate | 1.0 |
| 13 | Sodium benzoate | 2.0 |
| 14 | Sodium benzoate | 2.5 |
| 15 | Sodium benzoate | 3.0 |
| 16 | Sodium benzoate | 5.0 |
| 17 | Calcium propionate | 1.0 |
| 18 | Calcium propionate | 2.0 |
| 19 | Calcium propionate | 5.0 |
| 20 | Potassium sorbate | 1.0 |
| 21 | Potassium sorbate | 2.0 |
| 22 | Potassium sorbate | 2.5 |
| 23 | Potassium sorbate | 3.0 |
| 24 | Potassium sorbate | 5.0 |
| 25 | Sodium formate | 1.0 |
| 26 | Sodium formate | 2.0 |
| 27 | Sodium formate | 5.0 |
| 28 | Sodium nitrite | 5.0 |
| Plant Extracts: | | |
| 29 | Thujaplicin | 0.4 |
| 30 | Thujaplicin | 0.8 |
| 31 | Thujaplicin | 1.5 |
| 32 | Pine resin | 100.0 |

TABLE 4-continued

| Sample | Test Chemical | (% test chemical by weight unseasoned pine sample) |
|---|---|---|
| 33 | Soybean ester | 100.0 |
| Pharmaceuticals and Agricultural Fungicides: | | |
| 34 | Miconazole | 2.0 |
| 35 | Triazole | 3.0 |
| 36 | Triazole | 5.0 |
| 37 | Sodium triazole | 3.0 |
| 38 | Sodium triazole | 5.0 |
| 39 | Difluconazole | 2.0 |
| 40 | Clotrimazole | 1.0 |
| 41 | Voriconazole | 0.016 |
| 42 | Voriconazole | 0.031 |
| 43 | Voriconazole | 0.063 |
| 44 | Voriconazole | 0.125 |
| 45 | Thiabendazole | 0.0098 |
| 46 | Thiabendazole | 0.019 |
| 47 | Thiabendazole | 0.039 |
| Biocide Compositions Using Multi-component Solutions: | | |
| 48 | Borate-quat + thiabendazole[a] | 2.0 ± 0.1[b] |
| 49 | Borate-quat + Thujaplicin[a] | 0.05 |
| Controls: | | |
| 50 | Untreated Control | 0 |
| 51 | Ethanol Control | 70.0 |

[a]Tested on solid pine and pine OSB
[b]2.0% (by total weight) borate-quat solution combined with 0.1% (by total weight) thiabendazole The biocide compositions were tested for the efficacy in preventing mold fungal growth and compared to the abilities of the commercially used preservatives, fungicides, extracts, and pharmaceuticals in preventing mold fungal growth. The mold fungi used in the mold growth analysis include the mold fungi from Example 1. The mold fungi were prepared as in Example 1.

Specimens (7×20 millimeters cross section by 7 centimeters long) were cut from unseasoned southern yellow pine mill ends from a Mississippi sawmill and stored at 0° C. Average moisture content of the specimens was 48% by weight (n=3). Southern yellow pine oriented strand board (OSB) specimens (11×20 millimeters cross section by 7 centimeters long) were cut from a full sheet of OSB and conditioned to 70% relative humidity. Seven random replicate stakes were dip-treated for approximately 15 seconds in the sample compositions and held in a covered container overnight according to the ASTM standard test method D4445-91 (1998). Specimens were then arranged over four layers of blotting paper that was saturated with 30 milliliters DI water and a polyethylene mesh spacer in sterile disposable Petri dishes (150×25 millimeters) (commercially available from B-D Falcon, Los Angeles, Calif.). Untreated stakes were dipped in DI water and served as Control A for water-based test chemicals. Additional stakes were dipped in 70% (by weight) ethanol to serve as Control B for test chemicals of low solubility.

All stake samples were then sprayed with 1 milliliter of mold spore inoculum, sealed in polyethylene bags to prevent drying and incubated at 27° C. and 70% relative humidity for four weeks. Following incubation, stakes were individually rated for mold growth on a scale of 0-5 as in Example 1. The results are shown in Table 5.

TABLE 5

Mold Resistance Average Rating

| Sample: | A. niger | T. viride | P. chrysogenum |
|---|---|---|---|
| *Wood Preservatives and Additives:* | | | |
| 1 | 5.0 | 4.7 | 4.0 |
| 2 | 3.7 | 0.7 | 4.9 |
| 3 | 4.9 | 3.3 | 4.7 |
| 4 | 5.0 | 2.1 | 5.0 |
| 5 | 5.0 | 5.0 | 5.0 |
| 6 | 4.1 | 5.0 | 3.3 |
| 7 | 4.3 | 2.1 | 3.1 |
| 8 | 4.4 | 0.6 | 0.4 |
| 9 | 4.3 | 1.4 | 0.4 |
| 10 | 0.0 | 0.0 | 0.9 |
| *Food Preservatives:* | | | |
| 11 | 5.0 | 5.0 | 5.0 |
| 12 | 4.6 | 4.4 | 4.9 |
| 13 | 2.9 | 3.1 | 2.4 |
| 14 | 1.7 | 1.0 | 0.0 |
| 15 | 0.4 | 0.4 | 0.0 |
| 16 | 0.0 | 0.7 | 0.0 |
| 17 | 5.0 | 4.6 | 4.9 |
| 18 | 5.0 | 4.7 | 5.0 |
| 19 | 0.9 | 3.3 | 2.0 |
| 20 | 5.0 | 4.9 | 5.0 |
| 21 | 2.6 | 2.9 | 2.6 |
| 22 | 0.0 | 0.7 | 0.0 |
| 23 | 0.0 | 1.0 | 0.0 |
| 24 | 0.0 | 0.0 | 1.7 |
| 25 | 5.0 | 4.3 | 4.6 |
| 26 | 5.0 | 4.1 | 4.7 |
| 27 | 4.7 | 4.0 | 3.3 |
| 28 | 5.0 | 5.0 | 4.9 |
| *Plant Extracts:* | | | |
| 29 | 5.0 | 1.0 | 0.0 |
| 30 | 0.0 | 0.0 | 0.0 |
| 31 | 0.0 | 0.0 | 0.0 |
| 32 | 5.0 | 3.9 | 4.1 |
| 33 | 5.0 | 5.0 | 5.0 |
| *Pharmaceuticals and Agricultural Fungicides:* | | | |
| 34 | 0.0 | 0.0 | 0.0 |
| 35 | 5.0 | 5.0 | 5.0 |
| 36 | 4.6 | 4.9 | 3.6 |
| 37 | 5.0 | 5.0 | 5.0 |
| 38 | 4.0 | 2.1 | 2.4 |
| 39 | 5.0 | 5.0 | 4.7 |
| 40 | 5.0 | 3.7 | 3.4 |
| 41 | 0.0 | 2.4 | 0.0 |
| 42 | 0.0 | 1.3 | 0.0 |
| 43 | 0.1 | 0.4 | 0.0 |
| 44 | 0.0 | 0.1 | 0.0 |
| 45 | 0.0 | 2.5 | 0.0 |
| 46 | 0.0 | 0.0 | 0.0 |
| 47 | 0.0 | 0.0 | 0.0 |
| *Biocide Compositions Using Multi-component Solutions:* | | | |
| 48 | 0.0 | 0.0 | 0.0 |
| 49 | 0.0 | 0.0 | 0.0 |
| *Controls:* | | | |
| 50 | 5.0 | 5.0 | 5.0 |
| 51 | 5.0 | 5.0 | 5.0 |

As shown in Table 5, while many individual components, such as many of the azoles and thujaplicin were not effective in inhibiting mold fungal growth when used alone, the combined biocide compositions containing the Borate-quat plus either an azole component or thujaplicin completely inhibited *T. viride* and *P. chrysogenum* on southern yellow pin and pine OSB. As such, by combining components, the biocide compositions of the present disclosure had improved efficacy in inhibiting mold growth on both southern yellow pine and OSB. Specifically, the samples of biocide compositions using multi-component solutions of the present disclosure completely inhibited mold growth on both southern yellow pine and OSB.

Example 3

In this Example, biocide compositions including an azole component or thujaplicin were prepared and tested for their efficacy in preventing mold fungal growth.

To prepare the biocide compositions, a borate-DMCA base was prepared by combining: boric acid (5%), a borate component available from National Boraxx, Cleveland, Ohio; propionic acid (25%), available from JT Baker, Phillipsburg, N.J.; dimethylcocoamine (55%), a quaternary amine component mixture, available from Lonza, Inc., Fair Lawn, N.J.; and polyethylene glycol (15%), a stabilizer available from Sigma Chemical, St. Louis, Mo. The other various components that can be used in the biocide compositions of this Example are listed below:

Voriconazole (0.1%), an azole component, available from Pfizer, Inc., New York, N.Y.

Thiabendazole (0.1% concentration diluted in 70% ethanol), an azole component, available from Sigma-Aldrich Chemical, St. Louis, Mo.

Tebuconazole (0.1%), an azole component, available from Bayer Corporation, Pittsburgh, Pa.

Propiconaole (0.1%), an azole component, available from Janssen Pharmaceutical, Titusville, N.J.

Thujaplicin (isopropyltropolone) (0.5% concentration diluted in 70% ethanol), available from Cedarome Canada, Inc., Montreal, Quebec.

The various components and amounts of the components used in the biocide composition samples are shown in Table 6.

TABLE 6

| Sample | TREATMENT[a] (by total weight biocide composition) |
|---|---|
| 1 | 0.1% voriconazole |
| 2 | 0.1% thiabendazole |
| 3 | 0.5% thujaplicin |

[a]As noted above, each sample has a 2% (by total weight) borate-DMCA base, which is then supplemented with an azole component or thujaplicin.

The biocide compositions were first tested for the efficacy in preventing mold fungal growth. The mold fungi used in the mold growth analysis includes the mold fungi used in Example 1. The mold fungi were first prepared as discussed in Example 1 above.

Specimens (7×20 millimeters cross section by 7 centimeters long) were cut from unseasoned southern yellow pine mill ends from a Mississippi sawmill, unseasoned Douglas-Fir (commercially available from Weyerhaeuser Company, Federal Way, Wash.), and unseasoned aspen and stored at 0° C. Kiln-dried southern yellow pine specimens were cut to the same dimensions and stored at 27° C. and 70% relative humidity. Five random replicate stakes of each wood-based material were dip-treated for approximately 15 seconds in each biocide composition and held in a covered container overnight according to the ASTM standard test method D4445-91 (1998). Specimens were then arranged over four layers of blotting paper that was saturated with 30 milliliters DI water and a polyethylene mesh spacer in sterile disposable Petri dishes (150×25 millimeters) (commercially available from B-D Falcon, Los Angeles, Calif.). Untreated stakes were dipped in DI water and served as Control A for water-based test chemicals. Additional stakes were dipped in 70% (by weight) ethanol to serve as Control B for test chemicals of low solubility.

All stake samples were then sprayed with 1 milliliter of mold spore inoculum, sealed in polyethylene bags to prevent drying and incubated at 27° C. and 70% relative humidity for four weeks. Following incubation, the stakes were individually rated for mold growth on a scale of 0-5 as in Example 1.

Additionally, following the mold growth analysis, all specimens except the control samples treated with either tebuconazole or propiconazole were reinoculated and reevaluated for mold growth inhibition at four-week intervals. Moisture in the test apparatus was adjusted to provide 100% relative humidity and the specimen samples were incubated at 27° C. and 70% relative humidity. The results are shown in Table 7.

TABLE 7

| Treatment[a] | Specimen (Wood-based material) | Time (weeks) | Mold Resistance Average Rating | | |
|---|---|---|---|---|---|
| | | | T. viride | P. chrysogenum | A. niger |
| Sample 2 | | | | | |
| Thiabendazole | Aspen | 4 | 0.0 | 0.0 | 0.0 |
| | | 8 | 0.0 | 0.0 | 0.0 |
| | | 12 | 0.2 | 0.0 | 0.8 |
| | Douglas-fir | 4 | 0.0 | 0.0 | 0.0 |
| | | 8 | 0.0 | 0.0 | 0.0 |
| | | 12 | 2.4 | 0.8 | 0.4 |
| | Southern Yellow Pine (unseasoned) | 4 | 0.8 | 0.0 | 2.2 |
| | | 8 | 1.6 | 4.2 | 4.2 |
| | | 12 | 1.8 | 4.4 | 4.6 |
| | Southern Yellow Pine (kiln-dried) | 4 | 0.0 | 0.0 | 0.0 |
| | | 8 | 3.8 | 4.4 | 0.0 |
| | | 12 | 4.8 | 4.6 | 2.4 |
| Sample 1 | | | | | |
| Voriconazole | Aspen | 4 | 0.0 | 0.0 | 0.0 |
| | | 8 | 0.0 | 0.4 | 1.0 |
| | | 12 | 0.4 | 1.8 | 3.2 |
| | Douglas-fir | 4 | 0.0 | 0.0 | 0.0 |
| | | 8 | 0.2 | 0.0 | 0.0 |
| | | 12 | 1.0 | 5.0 | 4.0 |
| | Southern Yellow Pine (unseasoned) | 4 | 0.4 | 0.0 | 0.0 |
| | | 8 | 0.4 | 4.0 | 3.0 |
| | | 12 | 0.4 | 3.8 | 4.0 |
| | Southern Yellow Pine (kiln-dried) | 4 | 0.0 | 0.0 | 0.0 |
| | | 8 | 3.4 | 4.8 | 1.0 |
| | | 12 | 4.4 | 4.8 | 4.2 |
| Sample 3 | | | | | |
| Thujaplicin | Aspen | 4 | 0.0 | 0.0 | 0.0 |
| | | 8 | 1.8 | 0.8 | 0.8 |
| | | 12 | 2.0 | 1.4 | 2.6 |
| | Douglas-fir | 4 | 0.0 | 0.0 | 0.0 |
| | | 8 | 0.0 | 0.0 | 0.0 |
| | | 12 | 2.8 | 2.8 | 2.6 |
| | Southern Yellow Pine (unseasoned) | 4 | 2.6 | 0.6 | 1.4 |
| | | 8 | 3.4 | 3.6 | 4.8 |
| | | 12 | 3.6 | 4.2 | 4.8 |

TABLE 7-continued

| Treatment[a] | Specimen (Wood-based material) | Time (weeks) | Mold Resistance Average Rating | | |
|---|---|---|---|---|---|
| | | | T. viride | P. chrysogenum | A. niger |
| | Southern Yellow Pine (kiln-dried) | 4 | 0.0 | 0.0 | 0.0 |
| | | 8 | 4.4 | 3.6 | 1.8 |
| | | 12 | 4.4 | 3.4 | 4.4 |
| Control A | Aspen | 4 | 3.0 | 4.4 | 4.0 |
| | Douglas-fir | 4 | 4.4 | 3.2 | 2.8 |
| | Southern Yellow Pine (unseasoned) | 4 | 5.0 | 5.0 | 5.0 |
| | Southern Yellow Pine (kiln-dried) | 4 | 4.7 | 3.6 | 4.3 |

[a]As noted above, each sample has a 2% (by total weight) borate-DMCA base, which is then supplemented with an azole component or thujaplicin.

As shown in Table 7, after eight weeks, all biocide compositions were shown to inhibit the growth of the test mold fungi on Aspen and Douglas-fir. The azole-containing biocide compositions protected the kiln-dried pine from *A. niger* and unseasoned pine from *T. viride*.

Furthermore, a comparison of azole components was conducted by dip-treating five specimens of unseasoned southern yellow pine with the 2% borate-DMCA base containing either 0.1% (by total weight) tebuconazole or propiconazole. The mold growth analysis described above was repeated for the specimens treated with biocide compositions containing an azole component. The results are shown in Table 8.

TABLE 8

| Treatment[a] | Mold Resistance Average Rating | | |
|---|---|---|---|
| | T. viride | P. chrysogenum | A. niger |
| Tebuconazole | 4.2 | 1.8 | 0.6 |
| Propiconazole | 3.2 | 0.2 | 0.6 |
| Sample 1 | 0.4 | 0.0 | 0.0 |
| Sample 2 | 0.8 | 0.0 | 2.2 |
| Control A | 5.0 | 5.0 | 5.0 |

[a]As noted above, each sample has a 2% (by total weight) borate-DMCA base, which is then supplemented with an azole component or thujaplicin.

As shown in Table 8, all of the azole-containing biocide compositions provided some level of inhibition against mold growth. At the same concentration, however, voriconazole and thiabendazole provided greater protection from the mold fungi as compared to propiconazole and tebuconazole. This is due, in part, to the mode of action of voriconazole. Specifically, whereas many azoles rely on inhibition of several membrane-bound enzymes and membrane lipid biosynthesis as a mode of action, voriconazole specifically inhibits cytochrome P-450-dependent 14α-sterol demethylase (P-450$_{DM}$) as the mode of action.

Furthermore, the biocide compositions were evaluated for their long-term efficacy by measuring the retention rate of the biocide compositions by the specimen samples. Specifically, retention of the biocide composition was determined by weighing conditioned specimen samples pre- and post-dipping and calculating the average weight loss (e.g., amount of composition retained) during the 15-second dip based on the average volume of the specimen. Retentions were expressed as kilograms per cubic meter. The results are shown in Table 9.

TABLE 9

| Sample | Retention Rate (kg/m³) | | | |
|---|---|---|---|---|
| | Kiln-dried Pine | Pine unseasoned | Aspen unseasoned | Douglas-fir unseasoned |
| 1 | 2.34 | 2.19 | 0.52 | 0.46 |
| 2 | 1.89 | 0.83 | 0.56 | 0.54 |
| 3 | 1.76 | 1.28 | 0.49 | 0.56 |

As shown in Table 9, the Kiln-dried wood soaked up the biocide composition more readily as compared to the unseasoned woods. Despite having lower retention ability, all of the wood-based materials, even the materials having lower retention capabilities, were still protected from fungal growth when treated with the biocide composition.

Example 4

In this example, various samples of biocide composition were prepared and tested for their efficacy in preventing mold fungal growth, decay fungal growth, and termite infestation. The efficacies of the various biocide compositions were then compared to the individual components of the biocide composition and to an untreated control.

To prepare the biocide compositions, various amounts of components were added together. Specifically, a borate base was supplemented with various components. The borate base and the various components (and their commercial suppliers) used in the biocide compositions are listed below:

Boric acid (5%), a borate component, available from National Boraxx, Cleveland, Ohio;

Propionic acid (25%), available from JT Baker, Phillipsburg, N.J.;

Dimethylcocoamine (55%), a quaternary amine component, available from Lonza, Inc., Fair Lawn, N.J.; and 1,2-propanediol (15%), a stabilizer available from Sigma-Aldrich, St. Louis, Mo.).

Voriconazole (0.1%), an azole component, available from Pfizer, Inc., New York, N.Y.

Thiabendazole (0.1% diluted in 70% ethanol), an azole component, available from Sigma-Aldrich Chemical, St. Louis, Mo.

Thujaplicin (isopropyltropolone) (0.5% concentration diluted in 70% ethanol), available from Cedarome Canada, Inc., Montreal, Quebec.

The various components and amounts of the components used are shown in Table 10.

TABLE 10

| | TREATMENT | | |
|---|---|---|---|
| Sample | Borate Component (% by total weight biocide composition) | Azole Component (% by total weight biocide composition) | Additional Component (% by total weight biocide composition) |
| A | 2% Borate base | Voriconazole (0.1%) | 0 |
| B | 2% Borate base | Thiabendazole (0.1%) | 0 |
| C | 2% Borate base | 0 | Thujaplicin (0.5%) |
| D | 2% Borate base | 0 | 0 |
| E | 0 | Voriconazole (0.1%) | 0 |
| F | 0 | Thiabendazol (0.1%) | 0 |
| G | 0 | 0 | Thujaplicin (0.5%) |
| Control (untreated) | 0 | 0 | 0 |

The biocide compositions were first tested for the efficacy in preventing mold fungal growth. The mold fungi used in the mold growth analysis included the mold fungi used in Example 1. The mold fungi were prepared as in Example 1.

Specimens (7×20 millimeters cross section by 7 centimeters long) were cut from unseasoned southern yellow pine mill ends from a Mississippi sawmill and stored at 0° C. Average moisture content of the specimens was 48% by weight (n=3). Fifteen random replicate stakes were weighed, dip-treated for approximately 15 seconds in each biocide composition, and re-weighed to determine biocide retention level as discussed in Example 3 above. The treated specimens were then held in a covered container overnight according to the ASTM standard test method D4445-91 (1998). Three specimens for each biocide composition treatment were then arranged over four layers of blotting paper that was saturated with 30 milliliters DI water and a polyethylene mesh spacer in sterile disposable Petri dishes (150×25 millimeters) (commercially available from B-D Falcon, Los Angeles, Calif.). Untreated stakes were dipped in DI water and served as Control A for water-based test chemicals. Additional stakes were dipped in 70% (by weight) ethanol to serve as Control B for test chemicals of low solubility.

All stake samples were then sprayed with 1 milliliter of mold spore inoculum, sealed in polyethylene bags to prevent drying and incubated at 27° C. and 70% relative humidity for four weeks. Following incubation, stakes were individually rated for mold growth on a scale of 0-5 as in Example 1. The results are shown in Table 11.

TABLE 11

| Sample: | Mold Resistance Average Rating Southern Pine |
|---|---|
| A | 1.8 |
| B | 0.0 |
| C | 0.0 |
| D | 2.8 |
| E | 0.04 |
| F | 0.0 |
| G | 3.2 |
| Control (untreated) | 5.0 |

As shown in Table 11, biocide compositions containing combinations of a borate component, propionic acid, a quaternary amine component and either azole component or thujaplicin inhibited mold grow better than the untreated control or the individual components themselves.

In addition to the mold fungi analysis above, the biocide compositions were tested for their efficacy in preventing decay fungal growth and again compared to the individual components and an untreated control. The decay fungi used in the decay fungi analysis included the decay fungi used in Example 1. The decay fungi were prepared in the same manner as the decay fungi in Example 1 above.

To test the biocide compositions' abilities to inhibit decay fungal growth, soil block culture bottles were first prepared according to American Wood Preservers' Association (AWPA) E-10-01 (2003). Southern pine feeders were inoculated with two brown-rot fungus, *P. placenta* and *G. trabeum* and maple feeders were inoculated with one white-rot fungus, *C. versicolor*. Bottles were incubated at 27° C. and 70% relative humidity for three weeks until the fungus completely colonized each feeder. Pre-weighed 1×1×1 centimeter southern yellow pine blocks, conditioned at 27° C. and 70% relative humidity, were vacuum-treated for 40 minutes at 172 kPa with each biocide composition. Blocks were conditioned at 25° C. for seven days, propylene oxide-sterilized, placed on actively growing feeders, and incubated at 27° C. and 70% relative humidity for twelve weeks. Following incubation, surface mycelia were brushed from each block. The blocks were then oven-dried at 60° C. for twenty-four hours and reconditioned at 27° C. and 70% relative humidity to a constant weight. The blocks were weighed and the average percentage weight loss was calculated. The results of the decay fungi analysis are shown in FIG. 1.

As shown in FIG. 1, all three biocide compositions, the borate base, and voriconazole alone, inhibited decay by *P. placenta*, *G. trabeum*, and *C. versicolor* at the concentrations tested in this Example.

The biocide compositions were additionally evaluated for their ability to inhibit termite infestation. Specifically, numerous samples of the subterranean termite, *Reticulotermes flavipes* (Kollar), were collected in Janesville, Wis. for a termite bioassay.

To begin the termite bioassay, pre-weighed and pre-conditioned southern yellow pine blocks (1×1×1 centimeter) (n=5) were dip-treated with either the biocide compositions prepared above or the individual components. Five control samples were prepared by dipping blocks into DI water.

Each block was conditioned to ensure all solvent had dissipated prior to being subjected to a termite bioassay according to no-choice test procedure (ASTM 1998). Each block was then placed in a lidded test dish with 50 grams sand, 8.5 millimeters of DI water, and 1 gram of termites. The dishes were incubated at 27° C. and 80% relative humidity for four weeks. The dishes were examined after one and four weeks for tunneling and mortality. The mortality was scaled using a label of "none" (representing a mortality rating of 0%); "slight" (representing a mortality rating of from 1% to 33%); "moderate" (representing a mortality rating of from 34% to 66%) "heavy" (representing a mortality rating of from 67% to 99%); or "complete" (representing a mortality rating of 100%). At the end of the four-week test period, the blocks were removed from the dishes, cleaned, dried, re-conditioned and weighed to determine weight loss of the block, indicating the relative wood consumption of the block by the termites. Additionally, a visual rating of 10 (representing no attack); 9 (representing a light attack); 7 (representing a moderate attack); 4 (representing a heavy attack); or 0 (representing complete failure in inhibiting termite infestation), was recorded for each sample block. The results of these evaluations are shown in Table 12.

TABLE 12

| | Termite Bioassay | |
|---|---|---|
| Sample: | Attack Rating | Mortality Rating |
| A | 9.8 | Moderate |
| B | 9.8 | Moderate |
| C | 9.8 | Moderate |
| D | 8.6 | Slight |
| E | 0.0 | None |
| F | 0.0 | None |
| G | 0.0 | None |
| Control (untreated) | 0.0 | None |

As shown in Table 12, the biocide compositions combining the borate component and either the azole component or thujaplicin acted as repellents, causing moderate mortality rates, weight losses of 0.6% to 3.3%, and an average attack rating of 8.8 or higher.

Figure 2:
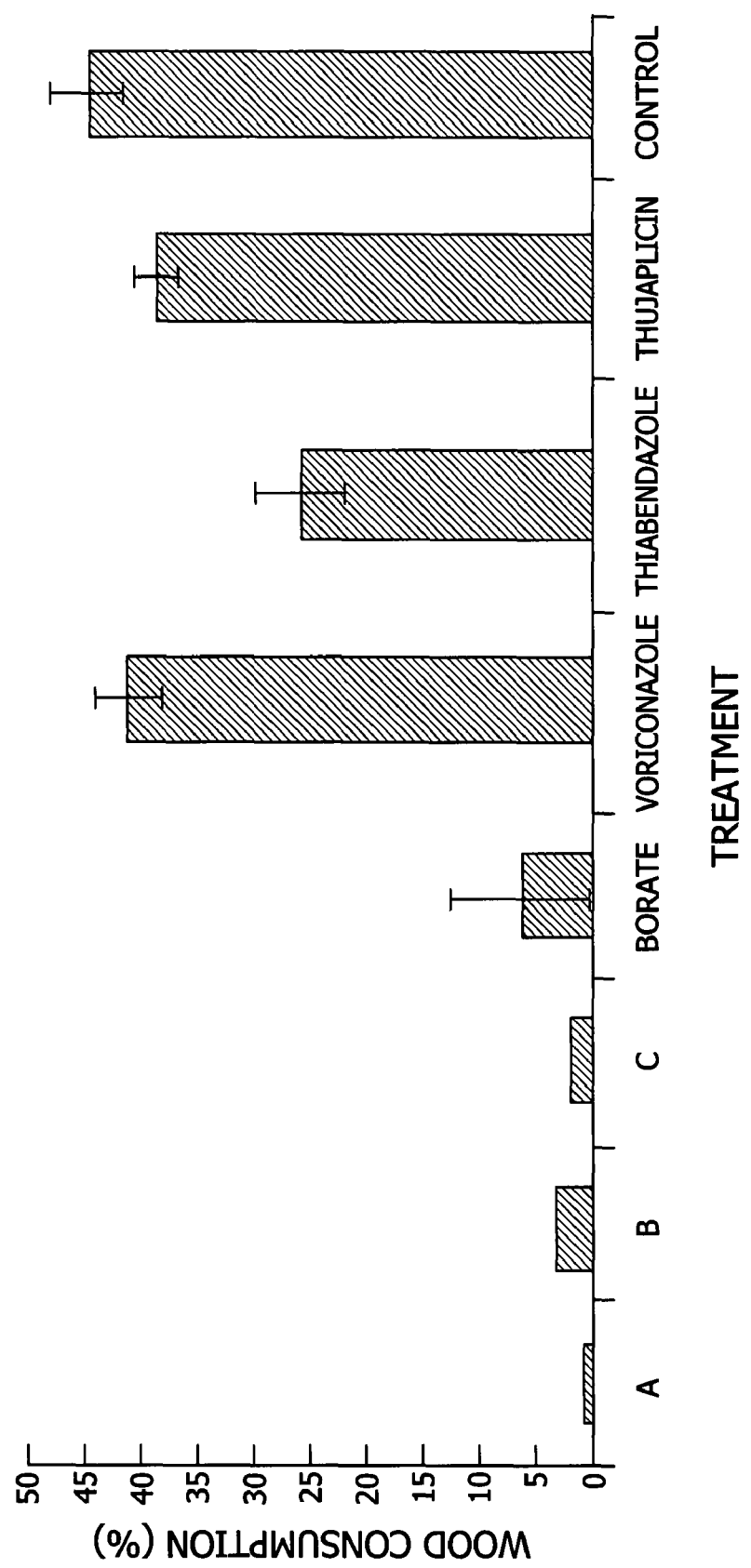
FIG. 2 is a graph depicting the weight loss of pre-treated and post-treated specimens, providing an indication of termite activity in the wood-based materials treated with the various biocide compositions of Example 4.

Additionally, the weight loss of pre-treated and post-treated specimens provided an indication of termite activity in the presence of the biocide compositions. As shown in FIG. 2, when using biocide compositions A, B, or C, wood consumption was significantly reduced as compared to the individual components and the control, indicating that the biocide compositions A, B, and C prevented the termites from consuming the wood specimens.

Example 5

In this Example, a biocide composition was prepared and evaluated for its retention and efficacy against mold fungal growth when applied by spray-coating, brush-coating, or dip-coating onto southern yellow pine.

Three samples of the biocide compositions were prepared and applied to southern yellow pine specimens conditioned as in Example 3 above. The biocide composition used for this Example was an aqueous solution including: 0.1% (by weight) boric acid, 0.1% (by weight) thiabendazole, 0.5% (by weight) propionic acid, 1.1% (by weight) dimethylcocoamine, and 0.3% (by weight) propylene glycol.

The biocide composition samples were evaluated for their long-term efficacy by measuring the retention rate of 2% (by weight) biocide composition on southern yellow pine specimens such as described more fully in Example 3. For the specimens that were treated by dip-coating, the specimens were treated as in Example 3 above. For the brush-coating and spray-coating specimens, a sufficient amount of aqueous solution containing the biocide composition was applied to the specimens by either brush-coating or spray-coating the specimens in order to wet all surfaces. The treated specimens were allowed to air-dry overnight at room temperature (e.g., 25° C.). Retention of the biocide composition was determined by weighing conditioned specimen samples pre- and post-application and calculating the average weight loss (e.g., amount of composition retained). Retentions were expressed as kilograms per cubic meter. The results are shown in Table 13.

TABLE 13

| Sample | Application Method | Retention Rate (kg/m$^3$) |
|---|---|---|
| 1 | Spray-coating | 0.537 |

TABLE 13-continued

| Sample | Application Method | Retention Rate (kg/m$^3$) |
|---|---|---|
| 2 | Brush-coating | 0.950 |
| 3 | Dip-coating | 0.830 |

As shown in Table 13, brush-coating or dip-coating specimens applied more biocide composition to the specimen and provided a more thorough coverage as compared to spray-coating.

Additionally, the biocide composition samples that were either brush-coated or spray-coated onto the specimens were then tested for their efficacy in preventing mold fungal growth. The mold fungi used in the mold growth analysis and analysis of the biocide compositions in preventing mold fungal growth are described in Example 1 above. The efficacies of the biocide composition samples were compared to the efficacy of southern pine specimens treated with 30 ml of DI water (either brush-coated (Control A) or spray-coated (Control B)). The results of the analysis are shown in Table 14.

TABLE 14

| | Application | Average Mold Rating | | |
|---|---|---|---|---|
| Sample | Method | A. niger | P. chrysogenum | T. viride |
| 1 | Spray-coating | 1.3 | 0.0 | 0.0 |
| Control B | Spray-coating | 5.0 | 5.0 | 5.0 |
| 2 | Brush-coating | 1.6 | 0.3 | 0.0 |
| Control A | Brush-coating | 5.0 | 5.0 | 4.0 |

As shown in Table 14, the biocide composition samples inhibited all types of mold fungi significantly better than the control sample. Specifically, both Control A and Control B failed to inhibit any mold fungi growth.

Example 6

In this Example, various concentrations of a biocide composition were evaluated for its ability to inhibit termite infestation. The ability of the biocide composition was then compared to the ability of disodium octaborate tetrahydrate, a borate component, alone and an untreated control to inhibit termite infestation. Specifically, samples of the subterranean termite, *Coptotermes formosans*, were collected at the Formosan Termite Research Facility at McNeill, Miss. for a termite bioassay.

To begin the termite bioassay, pre-weighed and pre-conditioned southern yellow pine blocks (1×1×1 centimeter) (n=5) were dip-treated with two concentrations of a biocide composition. A first control sample (Control A) was prepared by dipping blocks into DI water. A second control sample (Control B) was prepared by dipping the blocks into 0.28% (by weight) disodium octaborate tetrahydrate. The biocide composition included: 0.1% (by weight) boric acid, 0.1% (by weight) thiabendazole, 0.5% (by weight) propionic acid, 1.1% (by weight) dimethylcocoamine, and 0.3% (by weight) propylene glycol.

Each block was conditioned to ensure all solvent had dissipated prior to being subjected to a termite bioassay according to no-choice test procedure (ASTM 1998). Each block was then placed in a test dish with 1 gram of termites. Damp filter paper was placed into the lid of each dish to help maintain humidity during a four-week incubation at 27° C. and 80% relative humidity. The dishes were examined daily and mortality of the termites was recorded. At the end of the four-week test period, the blocks were removed from the dishes, cleaned, dried, re-conditioned and weighed to determine weight loss of the block, indicating the relative wood consumption of the block by the termites. The results of these evaluations are shown in Table 15.

TABLE 15

| Sample | Average Weight Loss (%) |
|---|---|
| Untreated Control A | 38.24 |
| Control B | 4.20 |
| 1 (2.0% (by weight) biocide composition) | 4.44 |
| 2 (4.0% (by weight) biocide composition) | 4.00 |

As shown Table 15, both samples of biocide composition prevented termite infestation of the wood-based specimens better than the untreated control.

Example 7

In this Example, a biocide composition was prepared and evaluated for its ability to prevent mold and decay fungal growth on an above-ground deck.

The biocide composition for use in this Example included: 0.1% (by weight) boric acid, 0.1% (by weight) thiabendazole, 0.5% (by weight) propionic acid, 1.1% (by weight) dimethylcocoamine, and 0.3% (by weight) propylene glycol.

Five (2 inches×6 inches×30 inches) long southern yellow pine deck boards were pressure-treated with the biocide composition using the pressure-treating method described more fully above.

After two years, there were no signs of decay, mold, or staining on any surface of the treated deck boards. Furthermore, the boards were rated sound with no evidence of weakening, softening, or discoloration from deteriorating organisms.

Example 8

In this Example, a biocide composition was prepared and evaluated for efficacy against mold fungi growth when applied by dip-coating onto five replicate southern yellow pine specimens. The efficacy of the biocide composition samples against mold fungal growth were then compared to untreated control samples.

The biocide composition was prepared and applied, at a concentration of 2% (by weight), to five southern yellow pine specimens conditioned as in Example 3 above. The biocide composition used for this Example included: 0.1% (by weight) boric acid, 0.1% (by weight) thiabendazole, 0.5% (by weight) propionic acid, 1.1% (by weight) dimethylcocoamine, and 0.3% (by weight) propylene glycol.

The treated specimens were evaluated for efficacy of the biocide composition on southern yellow pine specimens by the method described more fully below. Specifically, retention of the biocide composition was determined by weighing conditioned specimen samples pre- and post-application and calculating the average weight loss (e.g., amount of composition retained) during the 15-second dip based on the average volume of the specimen. The average retention rate for the five samples containing biocide composition was 0.47 g/cm$^3$.

Furthermore, the biocide composition samples were then tested for their efficacy in preventing mold fungal growth. The mold fungi used in the mold growth analysis included *Aureobasidium pullulans* (available from the Forest Products Laboratory, Madison, Wis.), *Aspergillus niger* 2.242 (available from University of Virginia, Charlottesville, Va.), and *Penicillium chrysogenum* PH02 (an isolate provided by Forest Products Laboratory, Madison, Wis.).

To test the efficacy of the biocide compositions in preventing mold fungal growth, the specimens above were held in a covered container overnight before being suspended vertically across the width of a test chamber over non-sterile soil that had been pre-inoculated with the mold fungi above. The test chamber was constructed according to ASTM D3273-00 specifications. Specimens were sprayed with 3×10$^7$ mold spores and held at 30° C. and 100% relative humidity for eight weeks. The specimens were rated individually for mold fungal growth on the following scale: 0=no growth; 1=20% growth; 3=60% growth; 4=80% growth; and 5=100% growth. The results of this analysis are shown in Table 16.

TABLE 16

| Sample | Treatment | Average Mold Rating |
|---|---|---|
| 1 | 2% (by wt.) biocide composition | 0.0 |
| 2 | 2% (by wt.) biocide composition | 0.0 |
| 3 | 2% (by wt.) biocide composition | 0.0 |
| 4 | 2% (by wt.) biocide composition | 0.0 |

TABLE 16-continued

| Sample | Treatment | Average Mold Rating |
|---|---|---|
| 5 | 2% (by wt.) biocide composition | 0.0 |
| 6 | Control | 4.0 |
| 7 | Control | 5.0 |
| 8 | Control | 5.0 |
| 9 | Control | 4.5 |
| 10 | Control | 5.0 |

As shown in Table 16, the samples of biocide composition inhibited the mold fungal growth significantly better than the control samples.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above biocide compositions and methods of using the compositions thereof without departing from the scope of the disclosure, it is intended that all matter contained in the above description and shown in the accompanying figures shall be interpreted as illustrative and not in a limiting sense.

What is claimed is:

1. A biocide composition comprising boric acid, thiabendazole, dimethylcocoamine, propionic acid, and propylene glycol.

* * * * *